(12) United States Patent
Sixto, Jr. et al.

(10) Patent No.: US 8,028,608 B2
(45) Date of Patent: Oct. 4, 2011

(54) TORQUE-LIMITING FASTENER DRIVER

(75) Inventors: Robert Sixto, Jr., Miami, FL (US); Juergen A. Kortenbach, Miami Springs, FL (US); Javier E. Castaneda, Miami, FL (US); Eduardo A. Ampuero, Miami, FL (US); Alfredo Castaneda, Miami, FL (US); Joel G. Marquart, Pembroke Pines, FL (US)

(73) Assignee: Depuy Products, Inc., Warsaw, IN (US)

( * ) Notice: Subject to any disclaimer, the term of this patent is extended or adjusted under 35 U.S.C. 154(b) by 158 days.

(21) Appl. No.: 12/419,339

(22) Filed: Apr. 7, 2009

(65) Prior Publication Data

US 2010/0251861 A1    Oct. 7, 2010

(51) Int. Cl.
B25B 23/153    (2006.01)
B25B 15/02    (2006.01)
A61B 17/58    (2006.01)

(52) U.S. Cl. .............................. 81/471; 606/104; 81/436
(58) Field of Classification Search .................... 81/471, 81/467, 477, 436, 177.6, 488; 606/104
See application file for complete search history.

(56) References Cited

U.S. PATENT DOCUMENTS

| | | | |
|---|---|---|---|
| 2,814,322 A | 11/1957 | Kupfrian | |
| 3,485,117 A | 12/1969 | Tyrell et al. | |
| 3,753,625 A * | 8/1973 | Fabrizio et al. | 81/177.6 |
| 4,041,811 A | 8/1977 | Durant | |
| 4,611,515 A | 9/1986 | Marbourg, Jr. | |
| 4,703,677 A * | 11/1987 | Rossini | 81/471 |
| 4,838,264 A | 6/1989 | Bremer et al. | |
| 5,123,313 A | 6/1992 | Andersson | |
| 5,176,050 A | 1/1993 | Sauer et al. | |
| 5,239,875 A | 8/1993 | Stasiek et al. | |
| 5,295,831 A | 3/1994 | Patterson et al. | |
| 5,347,894 A | 9/1994 | Fischer | |
| 5,433,665 A | 7/1995 | Beaty et al. | |
| 5,464,407 A | 11/1995 | McGuire | |
| 5,624,216 A * | 4/1997 | Detable et al. | 411/5 |
| 5,681,135 A | 10/1997 | Simonson | |
| 5,704,261 A | 1/1998 | Strauch et al. | |
| 5,746,298 A | 5/1998 | Krivec et al. | |
| 5,797,918 A | 8/1998 | McGuire et al. | |
| 5,868,047 A | 2/1999 | Faust et al. | |
| 6,132,437 A | 10/2000 | Omurtag et al. | |
| 6,155,147 A | 12/2000 | Dzieman | |
| 6,179,532 B1 | 1/2001 | Oldham | |
| 6,269,716 B1 | 8/2001 | Amis | |
| 6,308,598 B1 | 10/2001 | O'Neil | |
| 6,358,152 B2 | 3/2002 | Casutt | |
| 6,478,795 B1 | 11/2002 | Goumay et al. | |
| 6,487,943 B1 | 12/2002 | Jansson et al. | |
| 6,640,674 B1 | 11/2003 | Rinner et al. | |
| 6,752,808 B2 | 6/2004 | Schumacher | |
| 6,799,480 B1 | 10/2004 | Walsh et al. | |
| 7,107,883 B2 | 9/2006 | Casutt | |
| 7,188,556 B1 * | 3/2007 | Rinner | 81/467 |

(Continued)

Primary Examiner — Hadi Shakeri
(74) Attorney, Agent, or Firm — Gordon & Jacobson, PC

(57) ABSTRACT

A torque-limiting fastener driver for driving a bone fastener into bone includes a handle supporting a driver shaft. The driver shaft includes limited components which are designed to provide feedback to a user regarding the applied torsional force. In addition, the driver shaft is designed to controllably fail before any potential uncontrolled failure of the distal driving tip. This prevents application of too much torque and controlled design of the shape and size of the failed components.

5 Claims, 6 Drawing Sheets

U.S. PATENT DOCUMENTS

| | | |
|---|---|---|
| 7,243,580 B2 | 7/2007 | Frazee |
| 7,243,581 B1 | 7/2007 | Gao et al. |
| 7,272,999 B2 | 9/2007 | Cutler et al. |
| 7,331,263 B2 | 2/2008 | Erickson et al. |
| 7,334,509 B1 | 2/2008 | Gao et al. |
| 2004/0077409 A1 | 4/2004 | Lattuca et al. |
| 2005/0115368 A1 | 6/2005 | Prager et al. |
| 2005/0178253 A1 | 8/2005 | Karle |
| 2006/0016300 A1 | 1/2006 | Bubel |
| 2006/0149250 A1 | 7/2006 | Castaneda |
| 2006/0169090 A1 | 8/2006 | Kozak et al. |
| 2006/0179981 A1 | 8/2006 | Cutler et al. |
| 2006/0236826 A1 | 10/2006 | Cutler et al. |
| 2007/0289420 A1 | 12/2007 | Gao |
| 2008/0016990 A1 | 1/2008 | Rinner |

\* cited by examiner

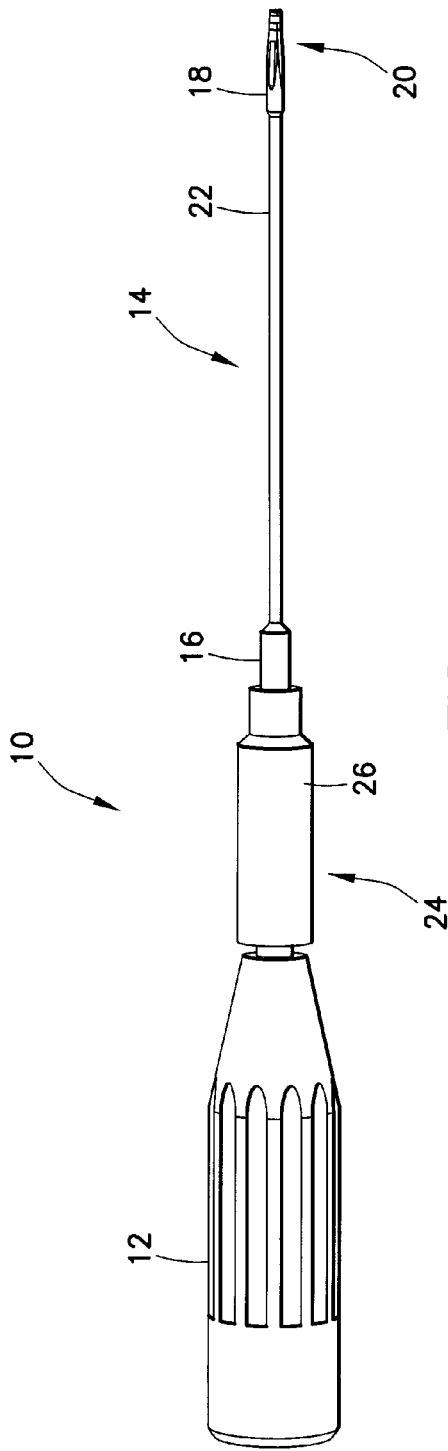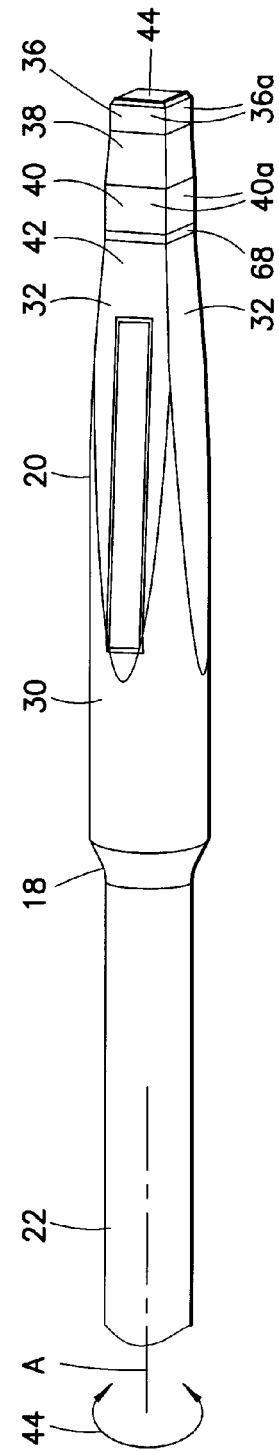

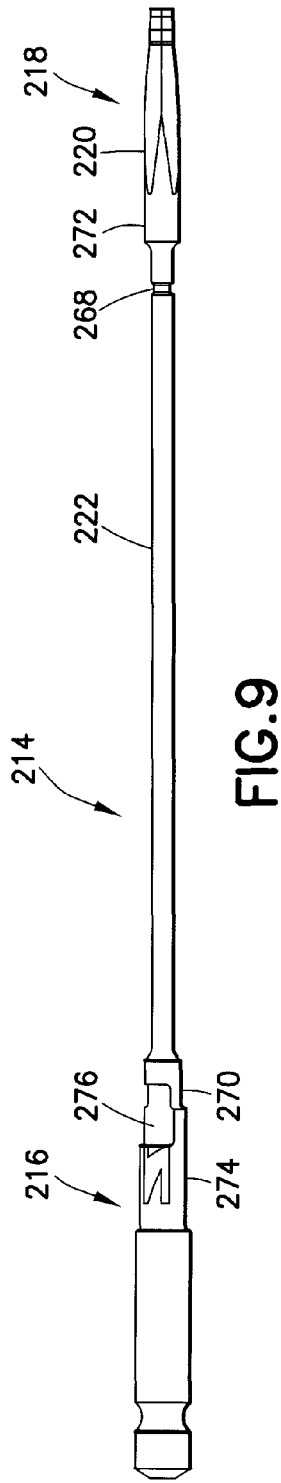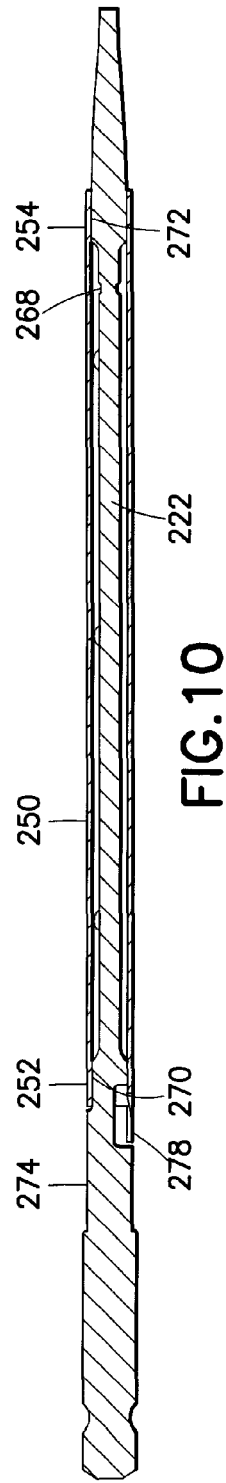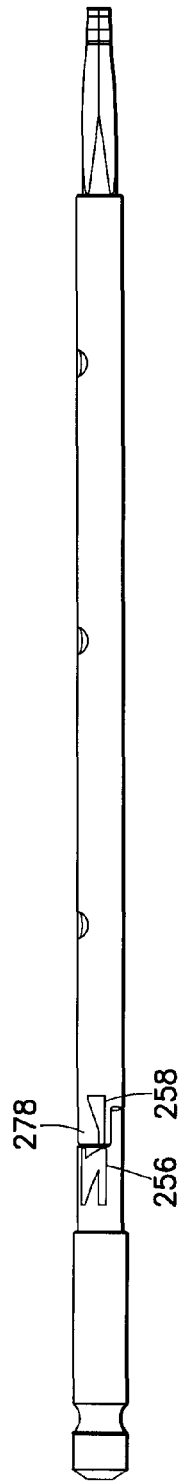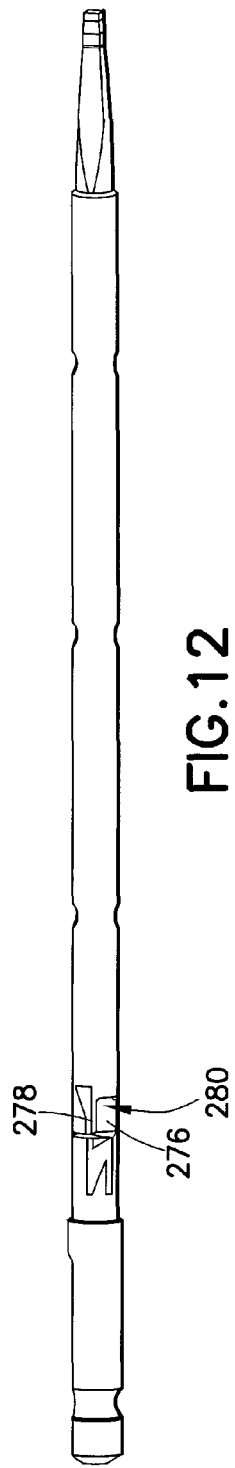

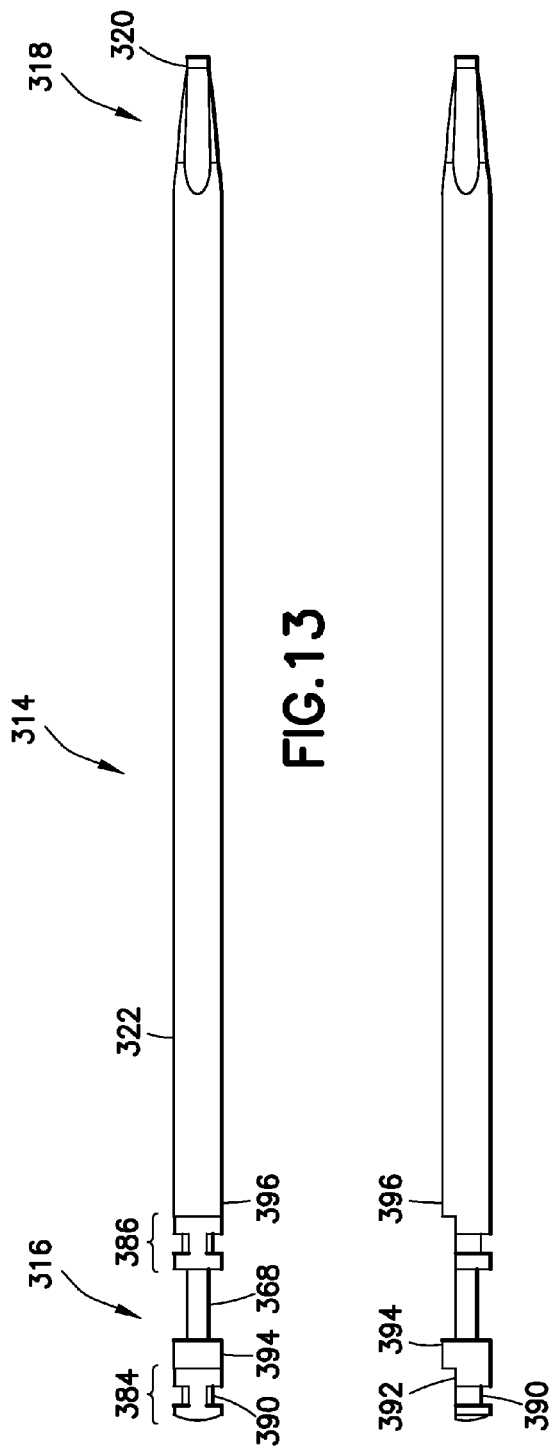
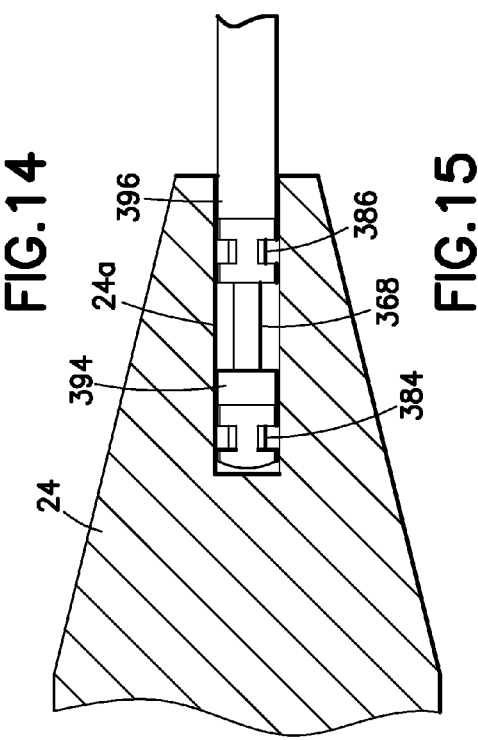
FIG. 13
FIG. 14
FIG. 15

TORQUE-LIMITING FASTENER DRIVER

FIELD OF THE INVENTION

This invention relates broadly to surgical instruments. More particularly, this invention relates to instruments for driving fasteners in orthopedic applications.

STATE OF THE ART

During some bone plating procedures, surgeons may have difficulty aligning the fastener driver with the bone plate fastener due to limited access, visualization, etc. If the driver tip is not properly engaged with the fastener head while attempting to drive the fastener into bone, there is danger of damaging the driver tip or the fastener head. Fastener drivers for driving very small fasteners, such as used for attaching small, low profile bone plates to bone, are especially susceptible to this type of damage.

During a plating procedure, the surgeon may use the fastener driver for several fasteners, resulting in accumulated wear of the driver tip. Therefore, it is also desirable to provide a sterile, low cost driver that may be discarded after use in one surgical procedure.

Further, fastener drivers are known which limit the torque that can be applied to the fastener that is being driven. Such torque-limiting drivers use some type of clutch or shear-pin mechanism in the driver shaft or handle and the mechanism comprises numerous components.

SUMMARY OF THE INVENTION

A fastener driver for driving a bone fastener into bone includes a handle and a driver shaft coupled to the handle in rotatably fixed manner. In a preferred embodiment, the driver shaft is removably attached to the handle. The driver shaft is a one-piece metal component having a proximal end coupled to the handle and a distal end configured into a driver tip for driving engagement with a head of a bone fastener. The driver shaft further includes an elongate middle portion stepped down in dimension from the proximal and distal ends. The middle portion has a longitudinal axis and is configured to bend elastically in any plane containing the longitudinal axis within a predetermined angular range. The middle portion also is configured to twist elastically within a predetermined angular range of twisting about the longitudinal axis when a predetermined torsional force is exceeded, thereby providing a tactile feedback to a user gripping the handle and operating the driver. According to one embodiment a visual indicator is also provided to reference the degree of twist to which the shaft is subject, and indicate whether the applied torque is within predetermined acceptable limits. According to a preferred aspect of the invention, a portion of the driver shaft is purposefully weakened to become a frangible segment and function as a fuse that controllably breaks at a predetermined location should the applied torque exceed a yield strength of the frangible segment under the applied torsional force. This ensures that any such breakage results in a dislocated piece of the driver shaft having a predetermined relatively non-injurious shape to the patient and of a sufficient size to be readily recovered from the surgical site.

Additional objects and advantages of the invention will become apparent to those skilled in the art upon reference to the detailed description taken in conjunction with the provided figures.

BRIEF DESCRIPTION OF THE DRAWINGS

FIG. 1 is a side elevation of a fastener driver according to the invention.

FIG. 2 is an enlarged isometric view of the distal end of the shaft of the fastener driver of FIG. 1.

FIG. 9 is a side elevation view of a driver shaft according to a second embodiment of the fastener driver.

FIG. 10 is a longitudinal section view of the driver shaft and tube of the embodiment shown in FIG. 9.

FIG. 11 is side elevation view of the driver shaft and tube of FIG. 10 shown in loaded low torque configuration.

FIG. 12 is a view similar to FIG. 11 shown when a maximum recommended torque is applied.

FIG. 13 is a side elevation view of the driver shaft of a third embodiment of a fastener driver.

FIG. 14 is a view similar to FIG. 13, rotated 90° about a longitudinal axis of the driver shaft relative to FIG. 13.

FIG. 15 is a broken longitudinal sectional view of the coupling of the handle to the shaft according to the third embodiment of the invention.

DETAILED DESCRIPTION OF THE PREFERRED EMBODIMENTS

Figure 3:
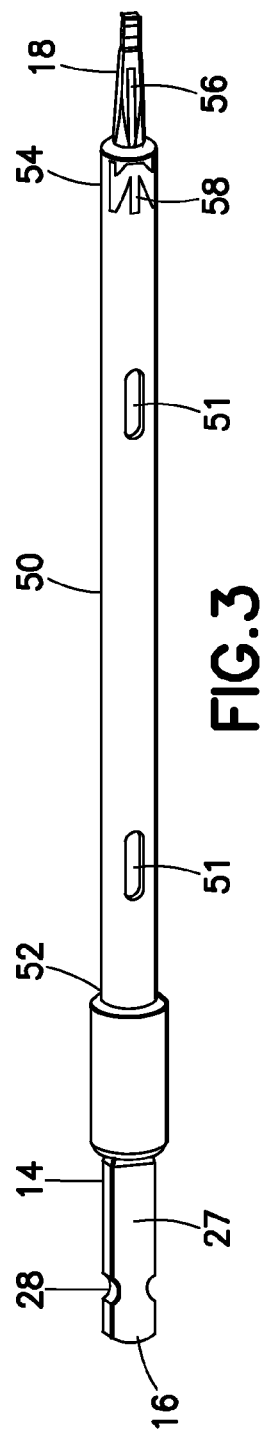
FIG. 3 is an isometric view of the shaft provided with a torque gauge in accord with the invention, shown in a neutral position.

Turning now to FIGS. 1 and 2, a torque-limiting fastener driver 10 for driving a bone fastener into bone is shown. The driver in the embodiment shown is particularly designed to drive small bone screws into low profile plates, such as to stabilize fractures in the hand. It is understood that the driver can be modified as necessary to drive bone fasteners for other orthopedic applications.

The driver 10 includes a handle 12 and a driver shaft 14 rotatably fixed relative to the handle. The driver shaft 14 is a once-piece metal component having a proximal end 16, a distal end 18 configured into a driver tip 20 for driving engagement with a head of a bone fastener, and a middle portion 22 between the proximal and distal ends. In a preferred embodiment, the shaft 14 is made from 440 stainless steel having a hardness of at least 48 RC. This material is chosen for its high tensile strength.

The proximal end 16 of the driver shaft 14 is preferably removably coupled to the handle 12 so that the shaft can be replaced within the handle as the driver tip 20 is worn from use. Well-known quick coupling mechanisms 24 can be used between the proximal end 16 and the handle 12, e.g., an AO connector releasable via a slidable collet 26. Referring to FIG. 3, for such engagement, the proximal end 16 of the shaft may include a longitudinally extending flat 27 and a partially circumferential groove 28. Alternatively, any other releasable coupling mechanism can be used with suitable structure provided to the shaft for the engagement. Moreover, as discussed in more detail below, the fastener driver is specifically designed with a limited number of components and in a manner permitting an inexpensive construction so that the entire driver can be discarded (both 12 handle and shaft 14)

once the driver tip 20 is no longer capable of stably driving screws; i.e., a single patient/procedure device.

Referring back to FIG. 2, the driver tip 20 of the shaft 14 includes a round proximal portion 30 which extends into facets 32 defining four sides extending towards a distal tip 34. The faceted portion includes, in distal to proximal order, a constant diameter first portion 36, a flared diameter second portion 38 extending from the first portion, a constant diameter third portion 40 extending from the second portion, and a flared diameter fourth portion 42 extending from the third portion. In the preferred embodiment, each of the first, second, third, and fourth portions 36, 38, 40, 42 have a square cross-sectional shape. The first portion 36 provides facets 36a that extend parallel in a longitudinal direction to provide high surface area contact against the sides of a recess for high transmission of torque. The first portion 36 also has a beveled end 44 to aid in guiding the tip 20 into the driver recess of a fastener. The flared second portion 38 interferes with the entry of the driver recess in a fastener to provide a temporary engagement therebetween to facilitate inserting or retrieving a fastener. The third portion 40 provides facets 40a that extend parallel in a longitudinal direction. The third portion 40 is sized larger than the first portion (in cross-section) and shaped to be readily received within and engage a tubular drill guide of the type adapted to be pre-assembled in plurality to a plate, such as the tubular drill guides disclosed in US Pub. No. 20060149250, which is hereby incorporated by reference herein in its entirety. The facets 40a provide regions of high surface area contact against the sides of the recess within such a tubular guide for high transmission of torque thereagainst for insertion or removal of the guide relative to a plate. The flared fourth portion 42 interferes with the entry of the tubular guide to provide a temporary engagement therebetween to facilitate removing a guide from the plate. It is appreciated that the driver tip 20 alternatively can be configured as a hex driver with six facets and the respective portions having a hexagonal shape. Other suitable non-circular cross-sectional shapes for driving orthopedic fasteners can also be provided in accord with the invention. 'Diameter' herein refers to the maximum cross-sectional dimension regardless of the cross-sectional shape.

The middle portion 22 of the shaft 14 has a length of 60-100 mm and more preferably approximately 80 mm. The middle portion 22 is reduced in cross-section dimension relative to the proximal end 16 and a proximal portion 30 of the driver tip 20. The middle portion is round in cross-section, and preferably 1.8 mm in diameter along its entire length. The middle portion has a longitudinal axis A extending throughout its length, and is configured to bend elastically in any plane containing the longitudinal axis within a predetermined angular range, e.g., ±20° relative to the axis A. The middle portion 22 also has inherent torsional flexibility such that it can twist elastically (in the direction of arrow 44) within a predetermined angular range of twisting about the longitudinal axis A when a predetermined torsional force is exceeded. The amount of twist is directly proportional to the torque applied to the driver. The twist is easily felt by the surgeon, thereby providing a tactile feedback to the surgeon gripping the handle and operating the driver. Further, once a user feels a twist, e.g., approaching 30°-40°, corresponding to greater than 7 in-lbs, such is sufficient feedback to indicate that torque should be reduced to prevent unintended driver tip breakage.

Figure 4:
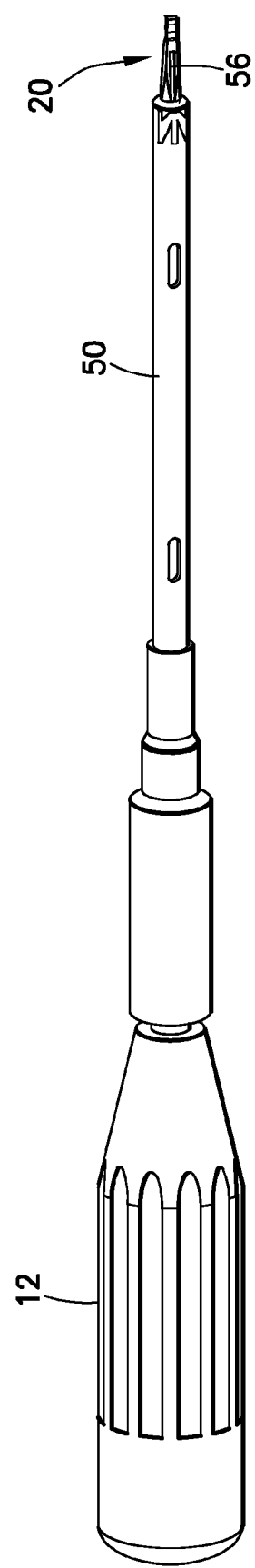
FIG. 4 is an isometric view of the fastener driver provided with the torque gauge and shown subject to a maximum acceptable torque.
Figure 6:
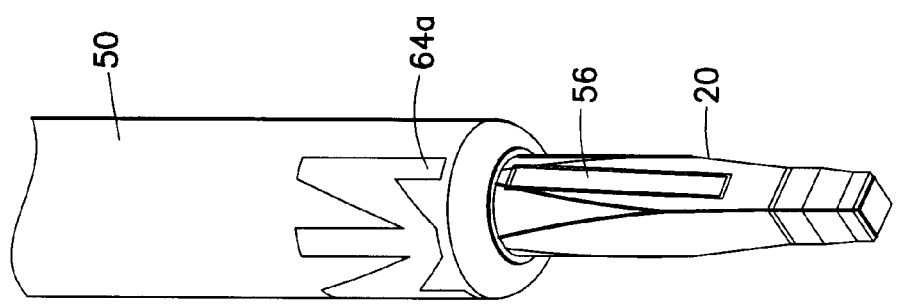
FIG. 6 is a view similar to FIG. 5, with the torque gauge indicating a maximum acceptable torque applied to the fastener driver.
Figure 5:
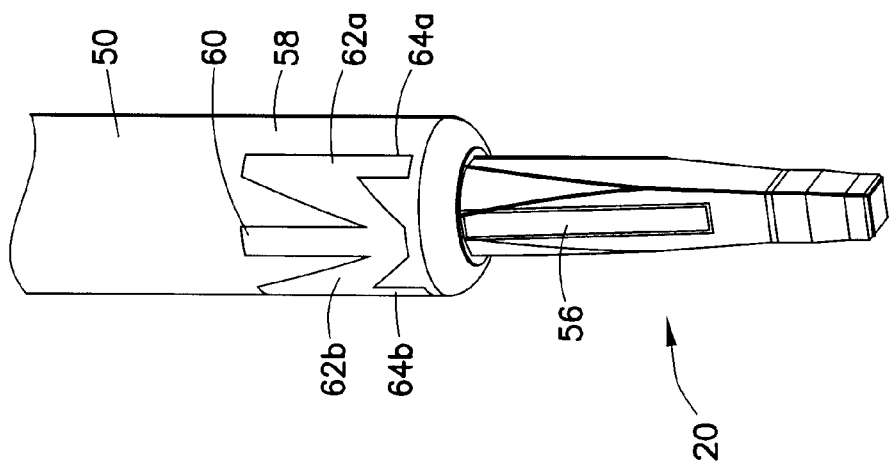
FIG. 5 is an enlarged view of the distal end of the shaft with a torque gauge.

Referring to FIGS. 3 and 4, optionally, a longitudinally stiff outer tubular member 50 is provided to the fastener driver over the shaft 14. The tubular member 50 includes a proximal end 52 and a distal end 54. The proximal end 52 of the tubular member 50 is rotational fixed to the proximal end 16 of the shaft 14. Alternatively, the tubular member 50 can be rotationally fixed directly to the handle 12. One or more venting holes 51 are provided along the length of the tubular member 50 to aid in sterilizing the driver during autoclaving. While the inclusion of the tubular member 50 limits the longitudinal flexibility of the driver, it permits further gauging the applied torque, as now described. The distal ends of the shaft and the tubular member 18, 54 include indicia, respectively 56, 58 that can be referenced against each other to provide a visual indication of the degree of twist to which the driver tip 20 of the shaft is torqued relative to the proximal end 16 of the shaft 14. The indicia 56 on the driver tip 20 is a longitudinally extending stripe. As seen best in FIG. 5, the indicia 58 on the tubular member 50 is a gauge including a central line 60 identifying 0 in-lbs torque (at rest), and flared indicators 62a, 62b leading to markings 64a, 64b of maximum acceptable limits of torque for both insertion and removal of a fastener. The maximum acceptable limit indicators 64a, 64b are preferably located 30°-40° on either side of the central line 60. By way of example, for a 1.3 mm fastener with a square driver, a preferred maximum acceptable torque causing alignment of the stripe 60 with the maximum torque line 64a is 10 in-lbs (FIG. 6).

Figure 7:
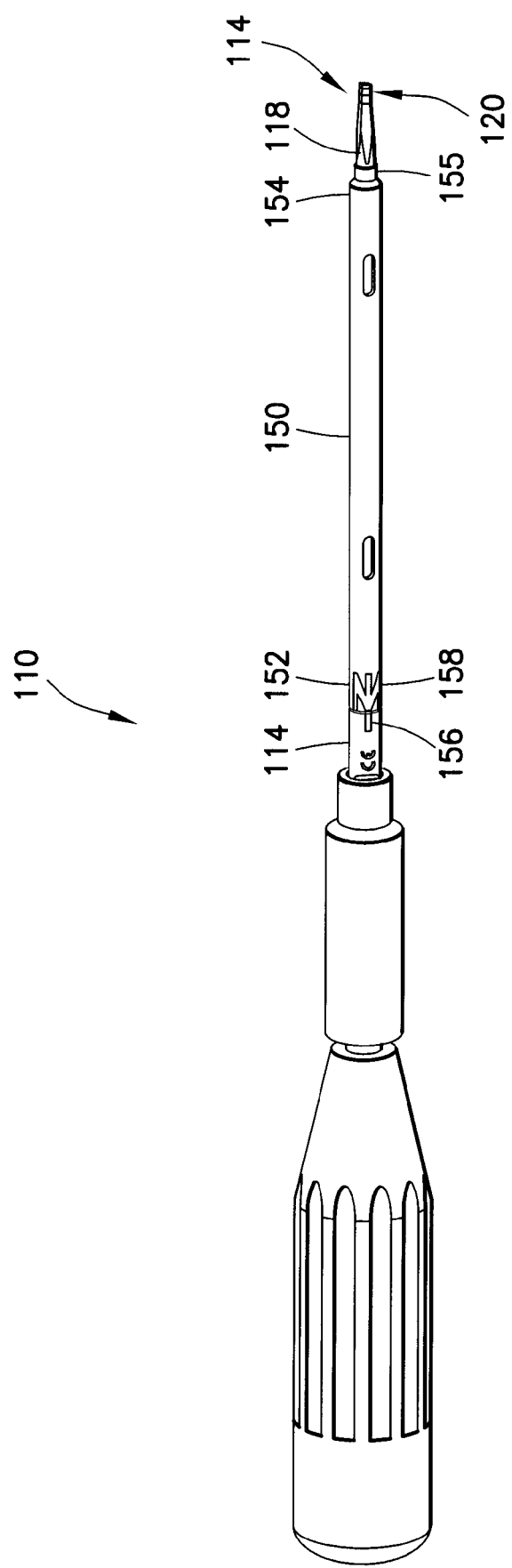
FIG. 7 is an isometric view of the fastener driver provided with the shaft having an alternate gauge.

Turning now to FIG. 7, another embodiment of the fastener driver 110 is shown with a driver shaft 114 provided with a tubular member 150. The distal end 118 of the shaft 114 and distal end 154 of the tubular member 150 are coupled together at 155 in a rotationally fixed manner. For example, ends 118, 154 can be crimped, welded or bonded together at 155. The proximal end 152 of the tubular member 150 is free to rotate relative to the proximal end 116 of the shaft 114. The tubular member 150 limits the bending of the shaft 114, thus reducing the stress on the shaft. The proximal ends of the shaft and the tubular member 116, 152 include indicia, respectively 156, 158 that can be referenced against each other to provide a visual indication of the degree of twist to which the driver tip 120 of the shaft is torqued relative to the proximal end 116 of the shaft 114. One of the indicia 156 is a longitudinally extending stripe and the other indicia 158 defines a gauge within which the stripe 156 is safely when the maximum acceptable limits of torque for both insertion and removal of a fastener are not exceeded. When the driver tip 120 is engaged with a fastener and the driver is operated to drive the fastener, the torsionally flexible middle portion of the shaft will twist causing the proximal end of the tubular member to rotate relative to the stationary portion of the shaft (as indicated by the indicia 156, 158 defining the gauge) in proportion to the amount of torque applied to the fastener.

Figure 8:
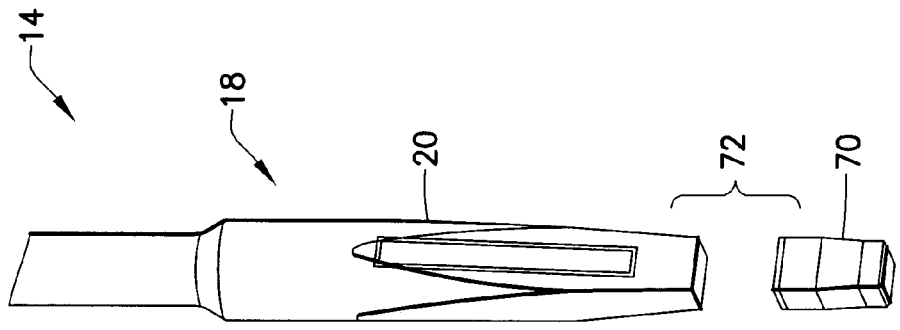
FIG. 8 is an enlarged view of the distal end of the shaft, illustrating the controlled breaking of the driver tip.

Referring now to FIGS. 2 and 8, the distal end 18 of the shaft 14, preferably at the driver tip 20, is provided with a frangible construct that causes separation of at least a portion 70 of the driver tip 20 from the shaft 14 should the applied torque during fastener insertion exceed a predetermined torsional limit, i.e., when the proximal end of the shaft is twisted by, e.g., up to a limit of 90°-120° relative to the distal end of the shaft (when corresponding, e.g., to 10 in-lbs or more), which is generally greater than a comfortable amount of angular rotation to be exerted by the surgeon. The frangible construct is formed by using wire electro-discharge machining (EDM) to define a circumferential groove 68 above the contact area between the driver tip 20 and the driver recess in the fastener. The EDM groove 68 is shaped and dimensioned to cause sudden failure and clean separation (shown at 72) along a predetermined fracture line when the yield strength for the driver tip is exceeded. This ensures that the applied torque cannot exceed too high a force, and any such breakage results in a dislocated piece of the driver tip having a predetermined relatively non-injurious shape to the patient, e.g., planar break, and of a sufficiently large size to be readily recovered from the surgical site.

Turning now to FIGS. 9 to 11, another embodiment of the torque limiting driver is provided. The driver shaft 214 includes a proximal end 216, a distal end 218 with a driver tip 220, and a middle portion 222 between the proximal and distal ends. A frangible segment 268 is formed as a necked down portion of the middle portion 222 of the shaft, preferably adjacent the driver tip 220. The frangible segment 268 is intended to function as a mechanical fuse and catastrophically fail if subject to an applied torque greater than a recommend torque for the intended use of the driver in a procedure, e.g., 10 in-lbs. A tube mount is defined on the shaft by cylindrical bearing portions 270, 272, each preferably of the same diameter, located relative to opposites ends of the middle portion 222 of the shaft 214. A larger cylindrical portion 274 is formed adjacent proximal portion 270, and a flat 276 is defined through both cylindrical portions 270, 274. The tubular member 250 extends over the shaft, closely contacting the shaft at the cylindrical bearing portions 270, 272 of the tube mount. The distal end 254 of the tubular member 250 is fixed to the distal cylindrical portion 272. The proximal end 252 of the tubular member includes a finger 278 extending therefrom. The middle portion 222 of the shaft is pre-twisted so that the finger 278 rotationally engages the flat 276 with a pre-load. The pre-load is preferably 7 in-lbs. A gauge, represented by indicia 256, 258 is provided to reference movement of the proximal shaft 216 relative to the finger 278 of the tubular member 250, and thus to gauge applied torque.

The tubular member, coupled about the cylindrical bearing portions 270, 272, carries the bending loads. This protects the shaft 214 (and frangible segment 268) from bending forces. The frangible segment 268 would otherwise be subject to premature failure due to the combination of applied torque and bending forces. The frangible segment 268 preferably has a round cross-section to facilitate control of its size and therefore its strength accurately.

In operation, the surgeon uses the driver as a standard driver. Provided the applied torque is less than the pre-load (7 in-lbs), the finger 278 remains in contact with the flat 276 during operation and the driver functions as if the shaft and tubular element are a unitary component. Referring to FIG. 12, should the applied torque be greater than the pre-load (i.e., greater than 7 in-lbs), the applied torque will overcome the pre-load and the shaft will twist defining a gap 280 between the finger 278 and the flat 276. The surgeon will feel the resulting springiness in the shaft, and the gauge 256, 258 will indicate the amount of applied torque within a recommended range. Should the applied torque be outside the recommended range and exceed a maximum permitted torque (e.g., 10 in-lbs), the frangible segment 268 will catastrophically fail causing portions of the shaft about the segment to separate from each other. The frangible segment 268 is structured so that the torque required to cause failure of the segment 268 is less than the torque that would cause failure of the driver tip 220 so as to ensure that the frangible segment 268 fails prior to the tip 220. In addition, after failure the separated pieces are long and easy to recover. A first piece includes the proximal end and middle portion of the shaft. A second piece includes the entire tubular member and distal end of the shaft fixed thereto. Therefore, recovery is not required to be performed from inside the surgical wound, as the proximal end of the both pieces will be readily obtainable from outside the surgical wound.

Turning now to FIGS. 13 through 15, another embodiment of a torque limiting driver is provided. The driver shaft 314 includes a proximal end 316, a distal end 318 with a driver tip 320, and a middle portion 322 between the proximal and distal ends. The middle portion 322 is not necessarily reduced in diameter relative to the proximal and distal ends 316, 318. The proximal end 316 is provided with a first connector 384, a second connector 386, and a reduced diameter frangible segment 368 between the first and second connectors 384, 386. The frangible segment 368 may be further reduced in diameter adjacent second connector 386 to facilitate a clean break thereat. Each of the first and second connectors 384, 386 includes structure permitting a quick connect driver handle 24 to releasably engage relative to the connector. For example, such structure on the connectors 384, 386 may include an at least partially circumferential recess 390 with a flat 392. In addition, bearing surfaces 394, 396 are provided on either side of the frangible segment 368. The walls 24a of the driver socket of the handle 24 define a tubular member that functions as the tubular member of prior embodiments, bearing against bearing surfaces 394, 396, and carrying the bending loads to thereby limit the frangible segment 368 to be subject only to torque.

In operation, the surgeon uses the driver to rotatably insert fasteners. Provided the applied torque is less than a maximum permitted torque (i.e., a torque that would cause failure of the frangible segment 368 (e.g., 10 in-lbs)), the driver functions as a standard driver. However, should the applied torque be greater than the maximum permitted torque, the frangible segment 368 will consistently/predictably fail. The frangible segment 368 is designed to fail prior to any failure of the driving tip 320. If the frangible segment 368 breaks during a surgical procedure, the surgeon is able to remove the driver shaft 314 and separated first connector 384 from the handle 24. The driver shaft 314 is re-inserted into the handle 24 with the handle then engaging the second connector 386 of the shaft. While the frangible segment 368 is designed to fail close to the second connector 386, the quick connect couplings of the handle are capable of functioning with a bit of 'slop' even should a portion of the segment 368 remain attached at the distal end of the second connector. Further, if necessary any remaining portion of the frangible segment 368 can be removed with a wire cutter prior to re-inserting the shaft. Re-insertion of the shaft 314 permits the surgeon to complete the procedure, albeit without the safety of the 'fuse' of the frangible segment 368.

The torque-limiting fastener driver of the invention has few components and is relatively low cost to manufacture. The shaft can be integrated with the handle for single-patient use or the shaft can be separable from the handle so that the handle can be used with replacement driver shafts. No complex mechanisms are required to monitor and/or limit the applied torque. In addition, the driver shaft may be provided in numerous sizes and with numerous styles of driver tips to accommodate different fasteners. However, the driver is particularly well-adapted to small drivers having corresponding small handles that cannot readily or cost-effectively accommodate torque limiting mechanisms.

There have been described and illustrated herein embodiments of a torque limiting fastener driver. While particular embodiments of the invention have been described, it is not intended that the invention be limited thereto, as it is intended that the invention be as broad in scope as the art will allow and that the specification be read likewise. Thus, while an outer tubular member attached at either the proximal or distal ends of the shaft has been disclosed for use as part of a torque gauge, it is appreciated that the gauge may be defined by an element other than a tubular member in conjunction with the shaft, e.g., a stiff wire coupled at one end of the shaft and referenced relative to a marking fixed relative to another end of the shaft. In addition, while particular materials, dimensions, and shapes have been disclosed, it will be understood that other suitable materials can be used and that the dimensions and shapes used should be appropriate for the orthopedic application and the fasteners to be driven. It will therefore be appreciated by those skilled in the art that yet other modifications could be made to the provided invention without deviating from its scope as claimed.

What is claimed is:

1. A driver shaft for coupling to a handle of a fastener driver for driving an orthopedic fastener into bone, consisting essentially of:
    a one-piece metal shaft having proximal and distal ends, and an elongate middle portion therebetween,
    said distal end defining a driver tip with a non-circular cross-sectional shape for driving engagement with the orthopedic fastener, said driver tip subject to mechanical failure at a first torque,
    said proximal end including,
        a first connector provided with an at least partially circumferential recess and a flat to couple said shaft to the handle of the fastener driver,
        a second connector provided with an at least partially circumferential recess and a flat,
        a first bearing surface and a second bearing surface,
        a frangible segment located between said first and second connectors and located between said first and second bearing surfaces, said frangible segment subject to mechanical failure at a second torque less than said first torque, wherein said second connector is adapted to couple said shaft to the handle of the fastener driver only once said first connector and at least a portion of said frangible segment are removed from said proximal end.

2. A fastener driver for driving an orthopedic fastener into bone, consisting essentially of:
    a user operable handle to apply a torque, said handle including a shaft coupler including a socket defining a wall; and a one-piece metal shaft having proximal and distal ends, and
    an elongate middle portion therebetween, said distal end defining a driver tip with a non-circular cross-sectional shape for driving engagement with the orthopedic fastener, said driver tip subject to mechanical failure at a first torque,
    said proximal end including a first connector to couple said shaft to said handle, a second connector on said shaft, a frangible segment located between said first and second connectors and subject to mechanical failure at a second torque less than said first torque, and bearing surfaces located on said shaft relative to opposite ends of said frangible segment such that when said shaft is received in said socket, said wall bears against said first and second bearing surfaces to carry bending loads across said frangible segment,
    said second connector adapted to couple said shaft to said handle once said first connector and at least a portion of said frangible segment is removed from said proximal end, and each of said first and second connectors includes an at least partially circumferential recess and a flat.

3. A fastener driver according to claim 2, wherein:
    said shaft coupler includes a location at which said first connector couples said shaft within said socket, and
    when said first connector and at least a portion of said frangible segment are removed from said shaft, said second connector is coupled within said shaft coupler at said location.

4. A fastener driver for driving an orthopedic fastener into bone, comprising:
    a user operable handle to apply a torque, said handle including a shaft coupler including a socket defining a wall; and
    a one-piece metal shaft having proximal and distal ends, and an elongate middle portion therebetween,
        said distal end defining a driver tip with a non-circular cross-sectional shape for driving engagement with the orthopedic fastener, said driver tip subject to mechanical failure at a first torque,
        said proximal end including a first connector at which said shaft is coupled to said shaft coupler at a first location in said socket, a second connector on said shaft, a frangible segment between said first and second connectors subject to mechanical failure at a second torque less than said first torque, and bearing surfaces located on said shaft relative to opposite ends of said frangible segment such that when said shaft is received in said socket, said wall bears against said first and second bearing surfaces to carry bending loads across said frangible segment, said second connector having structure to couple said shaft within said shaft coupler at said first location once said first connector and at least a portion of said frangible segment is removed from said proximal end and each of said first and second connectors includes an at least partially circumferential recess and a flat.

5. A fastener driver for driving an orthopedic fastener into bone, comprising:
    a one-piece metal shaft having proximal and distal ends, and an elongate middle portion therebetween,
        said distal end defining a driver tip with a non-circular cross-sectional shape for driving engagement with the orthopedic fastener, said driver tip subject to mechanical failure at a first torque,
        said proximal end including,
            a first connector provided with an at least partially circumferential recess and a flat to couple said shaft to the handle of the fastener driver,
            a second connector provided with an at least partially circumferential recess and a flat,
            a first bearing surface and a second bearing surface,
            a frangible segment located between said first and second connectors and located between said first and second bearing surfaces, said frangible segment subject to mechanical failure at a second torque less than said first torque, and
    a user operable handle to apply a torque to said driver shaft, said handle including a shaft coupler including a socket defining a wall, wherein said first connector couples within said shaft coupler at a first location, wherein said shaft is structured such that said second connector is torqueably engaged by said handle only after said first connector and at least a portion of said frangible segment are disengaged and/or are removed from said proximal end of said shaft.

* * * * *